Figure 1A:
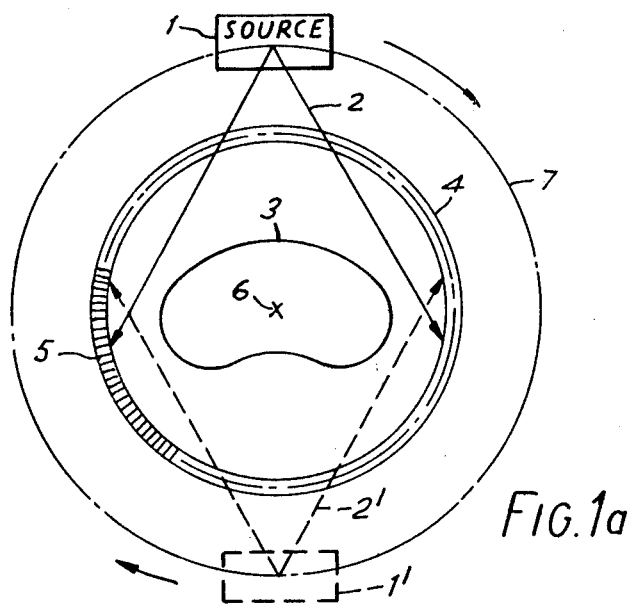

United States Patent [19]

Bagby

[11] 4,206,362

[45] Jun. 3, 1980

[54] MEDICAL RADIOGRAPHIC APPARATUS

[75] Inventor: John P. Bagby, Lake Forest, Ill.

[73] Assignee: E M I Limited, Hayes, England

[21] Appl. No.: 872,641

[22] Filed: Jan. 26, 1978

[51] Int. Cl.$^2$ .............................................. G03B 41/16
[52] U.S. Cl. ................................. 250/445 T; 250/360
[58] Field of Search ............................ 250/445 T, 360

[56] References Cited

U.S. PATENT DOCUMENTS 4,045,672  8/1977  Watanabe ........................ 250/445 T Primary Examiner—Craig E. Church Attorney, Agent, or Firm—Cooper, Dunham, Clark, Griffin & Moran

[57] ABSTRACT

In a computerized tomography (CT) apparatus, in which a fan-shaped X-ray distribution is rotated around the body of a patient, it is possible to use a ring of non-rotating detectors disposed to receive the radiation after passage through the body along a cross-sectional slice. The ring may be tilted and precessed axially so that detectors on the same side of the body as the source do not interrupt the radiation. A second source is disposed on the opposite side of the body to the first to irradiate the detectors when moved out of the radiation from the first and thereby to examine a second cross-sectional slice at the same time as the first slice.

9 Claims, 8 Drawing Figures

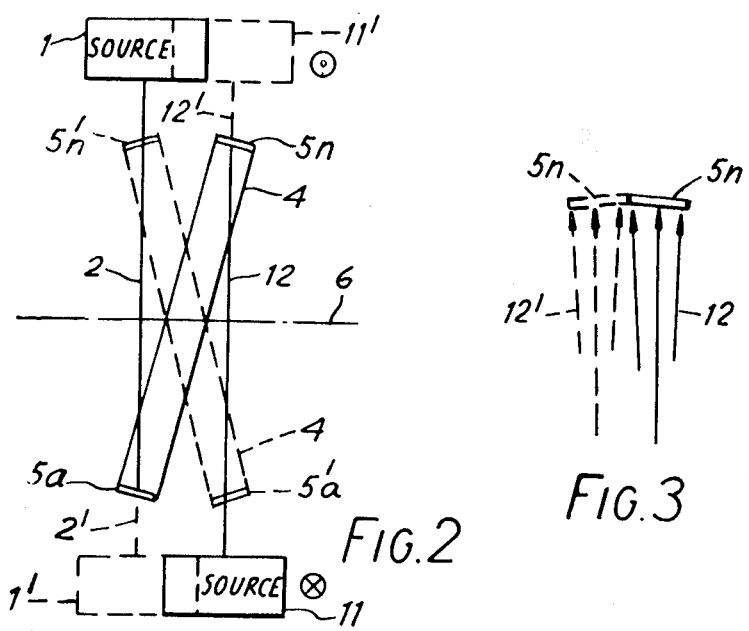
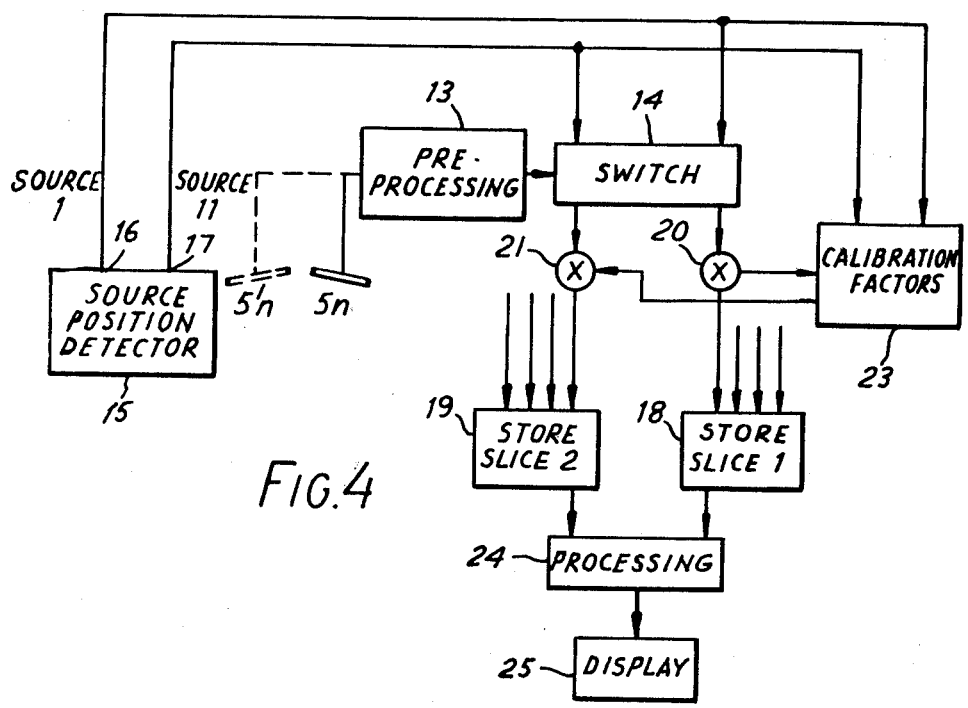

MEDICAL RADIOGRAPHIC APPARATUS

The present invention relates to medical radiographic apparatus and it especially relates to radiographic apparatus, known as computerised tomographic (CT) apparatus, which provides representations of the variation of absorption of penetrating radiation with position in cross-sectional slices of patient's bodies.

In U.S. Pat. No. 3,778,614 (Hounsfield) there are disclosed the principles of computerised tomography and several examples of apparatus for putting the principles into practice. The examples include apparatus in which a substantially planar fan-shaped distribution of radiation is rotated about a patient and the radiation distributed along a number of beams defined within the distribution is measured after emergence from the patient's body by a plurality of radiation sensitive detectors.

Such apparatus can be implemented using an array of detectors disposed on a circular path around the patient so that some of the detectors intercept the radiation throughout the rotation of the fan shaped distribution. In U.S. patent application Ser. No. 811,279, (R. W. Fetter, filed 29th June, 1977) which is incorporated herein by reference, there is disclosed a beneficial form of the apparatus in which the source of the planar distribution of radiation orbits about the patient, in the plane of examination, at a greater radius than the circular array of detectors. Those detectors on the opposite side of the patient to the source at any time are disposed in the plane of the radiation to allow the required measurements to be made. However, to prevent those detectors on the same side as the source from interrupting radiation incident on the body, application Ser. No. 811,279 provides that the detector ring becomes subject to a nutating motion which keeps the detectors out of the radiation path as necessary.

It is an object of this invention to provide a form of the apparatus described in the aforementioned patent application Ser. No. 811,279, which allows simultaneous examination of two closely spaced cross-sectional slices.

The invention provides a medical radiographic apparatus for investigating two cross-sectional slices of a patient's body, the apparatus including: two sources each for projecting a substantially planar fan-shaped distribution of radiation; locating means for locating the sources on opposing sides of the patient's body so that each source projects the radiation through a respective one of said slices; scanning means for orbiting the sources in synchronism about the patient's body so that the radiation is directed towards each slice from a plurality of directions; detector means comprising a ring of radiation detector devices; means for moving the detector ring substantially parallel to the axis of the source motion and in synchronism with that motion so that some of the detector devices intercept the radiation from one source after passage through the body and others of the detector devices intercept the radiation from the other source after passage through the body; and means for preventing motion of the detector ring in the direction of motion of the sources so that the radiation from each source is intercepted and measured by progressively different detector devices in the course of the orbital motion.

Figure 1B:
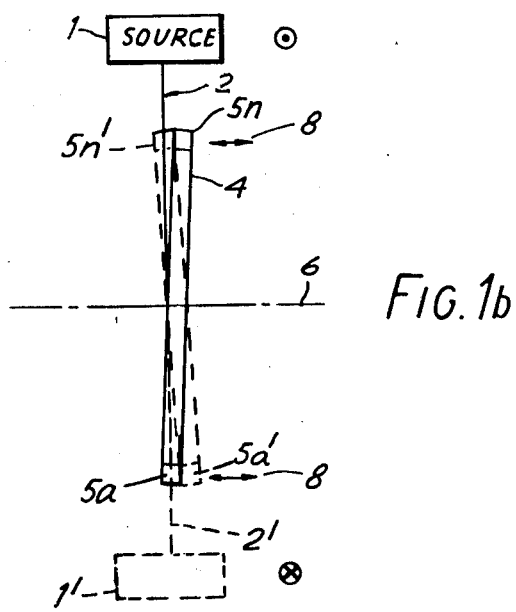
Figure 5:
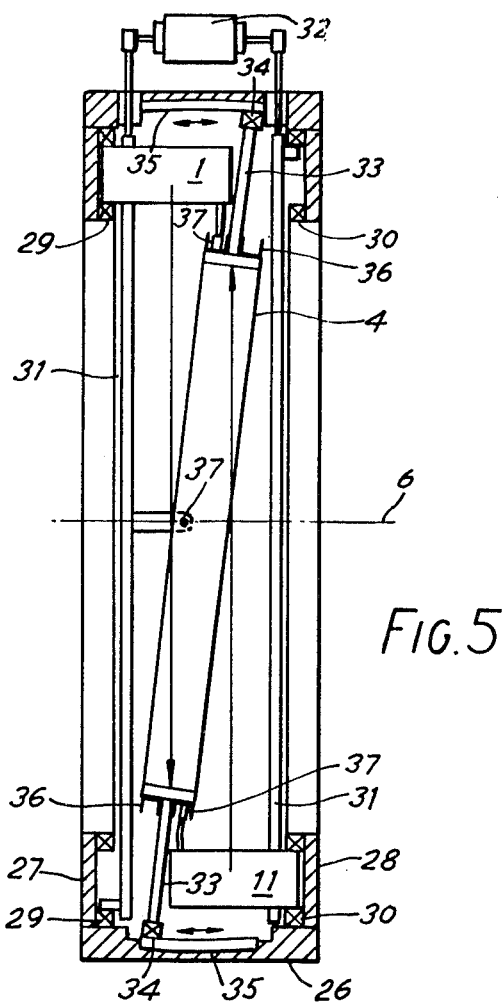
Figure 6A:
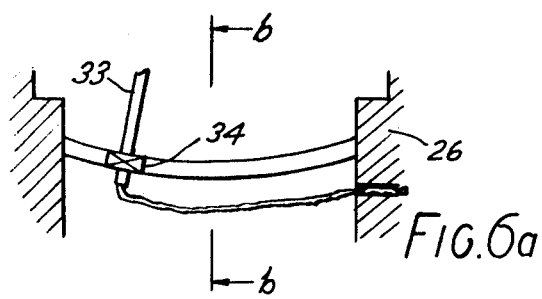
Figure 6B:
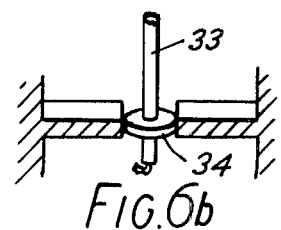

In order that the invention may be clearly understood and readily carried into effect examples thereof will now be described with reference to the accompanying drawings of which, FIGS. 1a and 1b show in simplified form the apparatus of application Ser. No. 811,279, FIG. 2 shows the principle of this invention, FIG. 3 illustrates different dispositions of detector devices, FIG. 4 shows a circuit for organising data provided by the apparatus, FIG. 5 shows an arrangement for achieving the desired scanning motions, and FIGS. 6a and 6b show details of a bearing construction for the FIG. 5 arrangement.

The operation of the apparatus disclosed in application Ser. No. 811,279 can be seen from the simplified drawings of FIG. 1a and 1b which are in end and side elevation respectively. A source 1 directs a fan distribution 2 of X-rays to irradiate a body 3 and then be incident on a detector ring 4. The detector ring 4 comprises a plurality of detector devices, of which only some are shown at 5, disposed in a circle about an axle 6. The source 1 is arranged to orbit about axis 6, through at least 180°, so that the origin of the radiation follows the locus 7. Apart from the position 1, one more position for the source, 1', is shown in broken outline with the radiation being shown at 2'. The detector ring is not subject to a rotary motion about axis 6 but is subject to a nutating motion indicated by the arrows 8. This ensures that for source position 1 detectors such as 5a, on the opposite side of the body, intercept the radiation and those such as 5n, on the same side, do not do so. Conversely for source position 1' detectors 5n' do not intercept the radiation and detectors 5n' do so. The detector ring 4 has a steady precessional motion so that for all source positions in a continuous orbit the radiation is only intercepted by detectors opposing the source. Suitable arrangements for achieving the desired motion are disclosed in application Ser. No. 811,279.

In the application of CT scanning it has proved useful to examine two substantially parallel cross-sectional slices simultaneously. This can be achieved by disposing two sets of detectors to intercept a greater extent of radiation or by using two sources moving together, with two sets of detectors. Such arrangements are not straightforward, however, for the nutating detector motion described.

This invention provides a suitable arrangement using a second source, providing a parallel substantially planar fan of radiation which is incident on the detectors in those positions in which they have been displaced out of the radiation from the first source. The arrangement is shown in side elevation in FIG. 2 in which the two planar distributions have been shown spaced to an exaggerated extent for the sake of clarity. As in FIG. 1b, source 1 irradiates detectors 5a of ring 4 while detectors 5n are displaced so as to not interfere with the radiation. The sources are in this example at a greater radius than the detector ring but that is not necessary. In addition a second source 11, displaced 180° from source 1 in rotation and also displaced along axis 6, directs a parallel fan distribution 12 of radiation to intercept detector ring 4 at detectors 5a. As can be seen from FIG. 2, radiation 12 necessarily misses detectors 5a. Sources 1 and 11 rotate in a fixed relation about axis 6 and the detector ring 4 performs a nutating motion as before so that 180° opposed detectors intercept radiation from the different sources. As before for source 1 at 1' radiation 2' intercepts detectors 5n' but misses detectors 5a'. Similarly radiation 12' from source 11' intercepts detector 5a' but misses detectors 5n'. Thus in the course of a complete rotation the detectors provide information for two parallel cross-sectional slices. From FIG. 1a it will be apparent that the radiation is not confined to the plane of FIG. 2 but has a significant extent out of that plane. It is necessary to ensure that all of the fan of radiation intercepts the respective detectors. Preferably the two examined slices are closely spaced as indicated in FIG. 3 so that the extent of the nutation is small but the angular spread of the radiation can be restricted as a compromise reached between the two factors.

Although the information of each slice must be kept distinct from that of the other, each can be processed in known manner, such as by the processing technique described in U.S. Pat. No. 3,924,129. To keep the information separated, the data from each detector must be routed to different storage depending on the source from which the radiation received originated. This can be achieved by a position sensor, such as known photocell/graticule combinations fitted to the source orbiting mechanism or the source drive, or alternatively by a sensor fitted to the nutating source ring to detect its current position. The sensor output is used in known manner to divert the detector output after amplification, integration, digital conversion etc. to storage for one slice or the other.

It will be apparent that the two sources 1 and 11 used will probably have different radiation characteristics, such as radiation frequency spectrum, and that consequently the detectors whih intercept radiation from both sources will provide different output signals for the same absorption according to the respective source. It is, however, usual to provide in CT processing calibration for source characteristics, to improve the quality of the final representation. Such calibration is readily achieved by taking measurements with a phantom body of known absorption to obtain correction factors by which the detector output signals are adjusted. For the present apparatus the calibration should be performed separately for each source and the factors thus derived kept in look-up tables for application as required.

The detector data organisation thus achieved is thus shown in block diagram in FIG. 4. The figure shows the output channel for detector 5n shown also in position 5n' in dotted outline. The actual nature of the detector itself is not indicated but it may be a scintillator with photomultiplier or photodiode or any other suitably sensitve detector of penetrating radiation. The output is taken via preprocessing circuits 13, comprising amplifiers etc., to a switch circuit 14. Circuits 14 receive inputs from source position detector unit 15, which comprises the aforesaid graticule/photocell units or similar, which take the form of a signal on output 16 if source 1 is in a range of positions opposite detector 5n and a signal on output 17 if source 11 is in those positions. The range of positions is, of course, the spread over which the detector is irradiated. The switch 14 responds to the position signals to route the data as appropriate to a store 18 for slice 1 and a store 19 for slice 2. If the detectors irradiated by opposed sources do not adjoin a signal may be provided to discard signals from intermediate detectors or those signals would be spurious noise and/or scatter signals. Alternatively these signals can be retained for calibration purposes. As they are routed to the respective stores the signals are multiplied, in multipliers 20 or 21 as appropriately, by the calibration factors for the respective source. These are held in (calibration factor) unit 23 which is a read only memory and output in response to the source position signals.

The stores 18 and 19 accumulate data from all detectors for their respective stores and provide them to a processing computer 24 for processing as referred to hereinbefore and display or storage at 25. Clearly the stores 18 and 19 can hold the data until it is all acquired. However for time saving they can provide the data to processing 24 on a time-sharing basis for parallel processing or the data for one slice can be processed on-line while the other is held for subsequent processing.

Arrangements for mounting a detector ring to allow the required nutating motion are described in the said U.S. patent application Ser. No. 811,279. These arrangements may be adapted to this invention, to ensure that the mounts do not interfere with the radiation from either source. Such adaptation will be apparent to the experienced engineer. FIG. 5 shows one alternative arrangement suitable for this invention. The figure is simplified to show the essential features and does not show many other features of a complete apparatus. The arrangement comprises a fixed ring-shaped main frame 26 having two end rings 27 and 28 and a centre part of larger aperture. The rings 27 and 28 carry ring bearings 29 and 30 respectively, in which sources 1 and 11 travel around the axis 6. Driving means are provided, to move the sources in their bearings, and also slip rings or appropriate cables for electrical and other connections. These can take suitable known forms although, since in this examples the two sources are not rigidly linked it is desirable that the drive means are appropriately synchronised to ensure that they maintain opposed positions. In this example each source carries a ring member 31, also supported at appropriate points by bearings 29 and 30. A respective drive belt passes over each of these rings 31 and both are driven by a single electric motor 32 mounted on main frame 26.

The detector ring 4 carries, radially disposed and oppositely one or, in this example, two rods 33. Each rod 33 carries at one end a bearing 34 by which it can move freely in a track 35, set in mainframe 26, in the direction shown in the arrows but is prevented from having a rotational motion. The mountings of bearings 34 on rods 33 are suitable to facilitate a small twisting motion about the axis of rods 33. The rods 33 also carry the detector output wiring, not shown in this Figure. FIGS. 6a and 6b, however, show a variation of the bearing arrangement for 34 and also how the detector wiring may be taken out. Other forms may readily be devised. For example other rods similar to 33, but not captured by tracks such as 35, may carry some of the detector wiring. They may be thin rectangular sections with the cable as flat ribbon. Alternatively they may be taken across the radiation of one source in which case the flat ribbon form will be particularly beneficial as obstructing the radiation less.

Ring 4 also carries two tracks 36, axially displaced from the locus of rods 33. Each source carries, suitably supported, a ball bearing runner 37 which runs in the appropriate track 36. The rings 31, discussed hereinbefore, may also carry one or two runners 37 at 90°.

In operation the sources are driven by motor 32, via the respective belt drives, to orbit around axis 6. During that rotation the runners 37 attached to each of the sources 1 and 11 support the detector ring 4 and rock it axially, on bearings 34 and tracks 35, so that it does not obstruct the radiation from the respective source. The movement is also effective to move the ring into the radiation from the other source. The runners 37 which lie midway between the two sources ensure that at those points the detector ring is centrally placed and provide further support. For smooth operation four sets of runners 37 are provided. Clearly, however, three would be sufficient. If a runner associated with one of the sources is dispensed with a single track 36 will suffice.

In an alternative form the runners 37 may be replaced by a race of many bearings linked at suitable points to source ring 31.

It will be seen that the support system described in FIG. 5, using rods 33, to prevent rotation of ring 4 does set the minimum axial spacing of the two sources so that the ring 4 needs to be more tilted than is otherwise necessary. The problem may be reduced by turning the source through 90° so that, unlike FIG. 5, the shortest dimension is axially disposed.

The detector outputs may also be taken off the ring 4 by slip rings. In a convenient, although complex, arrangement, the detector ring 4 can be slip ringed to one or other of two source supporting rings. These may in turn be slip ringed to the main frame.

It is known to be desirable in CT scanning for suitable collimation to be provided so that each detector receives substantially only radiation travelling directly from the source and not radiation scattered in the body. This obviates the need for calculations to be made to reduce caused by scattering. Clearly, in systems in which, angularly fixed detectors receive radiation from an orbiting source, each detector has to receive radiation incident from a plurality of directions.

To overcome this problem there is provided for each source, 1 or 11, a bank of collimators, not shown in the drawing, which point the detector apertures at the origin of the radiation and which orbit in synchronism with the source to maintain the correct relation. If only one source is provided, as in application Ser. No. 811,279, this collimator bank is mechanically linked to that source. In the present invention however the two sources are directly opposed in angle and are maintained in that relationship. It is therefore preferable that each source has fixed thereto a collimator bank to point the adjacent detectors at the opposing source.

Using two sources it is possible to analyse the chemical composition of the body tissue. In this so-called "Chemical Tomography" two sources of different characteristics are used to examine the same slice of the body. Comparison of the data provided for the two sources, taking into account the source characteristics, allows the required analysis. Since the two sources used in the arrangement described herein, examine closely adjacent slices it is possible to use them in this manner.

Preferably, however, for that purpose one or both of the two sources is supplemented by an additional source slightly displaced in angle about axis 6 but directing its fan of radiation in the same plane to be received by substantially the same detectors. Clearly these detectors would receive simultaneously radiation from two closely spaced sources. A means should be, therefore, provided to distinguish outputs resulting from the two sources. This can be achieved by switching the two sources in alternation and switching the output signals through different channels in synchronism with the source switching. Such alternate source opperation can be achieved with a source shutter that passes before one source and then before the other. It will be appreciated that the detector collimators should be appropriate to allow the detectors to see both of the sources in the respective plane.

This variant for chemical tomography is not restricted to the double planar scan described herein using three or four sources. It can also be applied using two sources in the same plane, instead of one in the single plane system of application Ser. No. 811,279 or other single plane systems.

What I claim is:

1. A medical radiographic apparatus for investigating two cross-sectional slices of a patient's body, the apparatus including: two sources each for projecting a substantially planar fan-shaped distribution of radiation; locating means for locating the sources on opposing sides of the patient's body so that each source projects the radiation through a respective one of said slices; scanning means for orbiting the sources in synchronism about the patient's body so that the radiation is directed towards each slice from a plurality of directions; detector means comprising a ring of radiation detector devices; means for nutating the detector ring in synchronism with the source motion so that some of the detector devices intercept the radiation from one source after passage through the body and others of the detector devices intercept the radiation from the other source after passage through the body; and means for substantially preventing motion of the detector ring in the direction of motion of the sources so that the radiation from each source is intercepted and measured by progressively different detector devices in the course of the orbital motion.

2. An apparatus according to claim 1 in which the ring of detector devices is of radius smaller than the orbital radius of the sources.

3. An apparatus according to claim 1 in which the means for nutating the detector ring comprises cooperating guide means on the detector ring and guide means associated with at least one of the sources.

4. An apparatus according to claim 3 including guide means associated with each source.

5. An apparatus according to claim 3 in which the cooperating guide means comprise at least one circumferential track, fixed in relation to one of the detector ring and at least one source, and runners, travelling in said track and fixed to the other of the detector ring and the at least one source.

6. Medical radiographic apparatus, for investigating two substantially parallel slices of a patient's body, the apparatus including two sources of penetrating radiation, such as x-radiation, each providing a fan-shaped distribution of the radiation; locating means for locating the sources on opposite sides of the patient's body and disposed in relation to the body so that each source projects radiation through a respective one of said slices; scanning means for rotating the sources in synchronism around the patient's body so that each directs radiation through its respective slice from a plurality of directions; detector means comprising a plurality of detector elements, sensitive to the radiation, disposed along a circular path surrounding the patient's body, the detector elements substantially immobile in the direction of rotation of said source; means locating the detector means so that the circular path is closer to the patient's body than the loci of rotation of the sources; and means for moving the detector elements such that elements disposed on the same side of the body as a source do not intercept the radiation emitted by that source but do intercept the radiation transmitted through the body after emission by the other source.

7. Medical radiographic apparatus, for investigating cross-sectional slices of the body of a patient, the apparatus including: a source of a fan-shaped distribution of penetrating radiation, such as x-radiation, disposed to direct the radiation to irradiate the body along a cross-sectional slice; scanning means for moving the source around the body to irradiate the cross-sectional slice from a plurality of different directions; detector means comprising a plurality of detector devices, sensitive to the radiation, disposed along an arcuate path of smaller radius than the locus of the source motion, surrounding the body; means for restraining the detector devices to be substantially immobile in the direction of motion of the source; means for moving detector devices for the time being disposed at the same side of the body as the source, so that they do not interrupt the detection of said radiation by detector devices for the time being disposed at the opposite side of the patient's body to said source; and a further source of a fan-shaped distribution of radiation, disposed on the opposite side of the body to the first source and also moved by the scanning means in synchronism with the first source, to irradiate a second cross-sectional slice such that the radiation is incident on and detected by those detectors for the time being moved out of the radiation from the first source and is not intercepted by those detectors disposed in the radiation from the first source.

8. A medical diagnostic X-ray machine for examining a patient comprising:

means for passing penetrating radiation through a first sectional slice of the patient from each of a first plurality of locations distributed along a first locus which extends at least half way around the patient and for passing penetrating radiation through a second sectional slice of the patient from each of a second plurality of locations distributed along a second locus which also extends half way around the patient;

means for detecting the penetrating radiation, said detecting means surrounding the patient and being closer to said slices than said first and second loci; and means for moving the detecting means to cause successive portions of the detecting means to view successively each location of said first plurality of locations to receive radiation travelling along a first set of paths which go through the first slice and intersect the detecting means only once and to cause other successive portions of the detecting means, angularly spaced from said first mentioned portions, to view successively each location of said second plurality of locations to receive radiation travelling along a second set of paths which go through the second slice and intersect the detecting means only once.

9. A medical diagnostic X-ray machine as in claim 8 including means for deriving a first set and a second set of signals related to the penetrating radiation received by the detecting means along said first set and said second set of paths, respectively, and for utilizing said first set and said second set of signals to form and display X-ray pictures of the first slice and the second slice, respectively.

* * * * *

UNITED STATES PATENT AND TRADEMARK OFFICE
CERTIFICATE OF CORRECTION

PATENT NO. : 4,206,362
DATED : June 3, 1980
INVENTOR(S) : John P. Bagby

It is certified that error appears in the above-identified patent and that said Letters Patent are hereby corrected as shown below:

Column 2, line 21, delete "axle" and insert --axis--;

line 32, delete "5n'" and insert --5a'--;

line 62, delete "5a" and insert --5n--;

Column 5, line 65, delete "opperation" and insert --operation--;

Column 6, line 62, after "elements" insert --being--.

Signed and Sealed this

Eleventh Day of January 1983

[SEAL]

Attest:

GERALD J. MOSSINGHOFF

Attesting Officer

Commissioner of Patents and Trademarks